United States Patent [19]
Hauser et al.

[11] 4,205,688
[45] Jun. 3, 1980

[54] METHOD AND APPARATUS FOR DEVELOPING AND MEASURING PULSED BLOOD FLOW

[75] Inventors: Herbert H. Hauser, New York, N.Y.; Marie-Lucienne Tannieres, Paris, France

[73] Assignee: Doll Research, Inc., New York, N.Y.

[21] Appl. No.: 799,218

[22] Filed: May 23, 1977

[51] Int. Cl.² ............................................. A61B 5/02
[52] U.S. Cl. .............................. 128/694; 73/194 EM
[58] Field of Search ................... 128/2.05 A, 2.05 F, 128/2.05 C, 2.05 M, 2.05 V, 327, DIG. 3, 2.1 Z, 691–694; 364/415–417; 73/194 M, 194 EM

[56] References Cited

U.S. PATENT DOCUMENTS

| 3,482,565 | 12/1969 | Gowen | 128/2.05 A |
| 3,527,204 | 9/1970 | Lem et al. | 128/2.05 A X |
| 3,552,383 | 1/1971 | Krueger | 128/2.05 A X |
| 3,847,142 | 11/1974 | Williams, Jr. et al. | 128/2.05 F |
| 3,920,004 | 11/1975 | Nakayama | 128/2.05 A X |
| 3,994,285 | 12/1974 | Doll | 128/2.05 F |
| 3,996,924 | 12/1976 | Wheeler | 128/2.05 V |
| 3,996,925 | 5/1975 | Djordjevich | 128/2.05 V |
| 4,030,485 | 6/1977 | Warner | 128/2.05 A |
| 4,116,230 | 9/1978 | Gorelick | 128/2.05 M |
| 4,134,396 | 1/1979 | Doll | 128/2.05 F |

FOREIGN PATENT DOCUMENTS

| 1185443 | 3/1970 | United Kingdom | 128/2.05 V |
| 1340542 | 12/1973 | United Kingdom | 128/2.05 V |
| 1426319 | 2/1976 | United Kingdom | 128/2.05 V |

OTHER PUBLICATIONS

Swan, K. G. et al., "A Miniature Occluder for Electromagnetic Blood Flow Measurements," Jrnl. of TCV Surgery, vol. 63, #3, Mar. 1972, pp. 403–407.
Darling, R. C. et al., "Quantitative Segmental Pulse Volume Recorder: A Clinical Tool" Surgery, vol. 72, No. 6, pp. 873–887.
Degowin & Degowin, "Diagnostic Examination," MacMillan & Co., 1965, pp. 384–389.

Primary Examiner—Robert W. Michell
Assistant Examiner—Francis J. Jaworski
Attorney, Agent, or Firm—Kenyon & Kenyon

[57] ABSTRACT

A blood flowmeter responsive only to the pulsatile component of blood flow is combined with apparatus for converting normal blood flow in a limb to fully pulsated flow to provide accurate zero baseline and total flow information. Preferably, the arterial flow in a limb is fully pulsatized by inflating a pressure cuff, which surrounds the limb on the distal side of a flow sensor location, to a pressure at or slightly above the local diastolic pressure. Arterial flow in the limb is thereby occluded during the diastolic and post-diastolic period of each heart cycle, preventing any flow that otherwise typically occurs during this period. The resulting pulsatile flow during the higher pressure systolic period will increase to compensate for any lost residual forward flow during the post-diastolic period; so that the total net forward flow with the cuff pressurized is approximately the same as the total net forward flow without the cuff pressurized. The altered flow is totally pulsatile, however. Subtraction of the integrated flow measured without cuff pressure from the integrated flow measured with the cuff pressurized yields a value approximately equal to any residual diastolic flow, which otherwise could not be measured by certain non-invasive magnetic flowmeters.

14 Claims, 4 Drawing Figures

METHOD AND APPARATUS FOR DEVELOPING AND MEASURING PULSED BLOOD FLOW

BACKGROUND OF THE INVENTION

1. Field of the Invention

The present invention relates to measurement of arterial blood flow in the limb of a living being, and particularly to an improved apparatus and method for measuring total net blood flow and determining an accurate zero flow level adapted for use with a non-invasive type of flowmeter responsive only to pulsatile flow.

The normal flow of blood through the arteries of a living being can be divided into variable and steady components. The variable component usually is called pulsatile flow, modulated flow, or AC flow (by analogy to electric current). The steady component is called non-modulated, residual, or DC flow. The pulsatile flow component can be further subdivided into forward flow (outward from the heart to the extremities) which occurs during the systolic period of the heart cycle, and reverse (retrograde) flow, which may occur during the diastolic period.

Due to the elasticity of the blood vessels, there is typically a small, fairly steady residual forward flow during the post-diastolic period. This constant, or non-modulated, residual flow can comprise a significant percentage of the total net forward flow during each heart cycle. The total net forward flow is the algebraic sum of the pulsatile systolic and steady residual forward flows and the pulsatile diastolic reverse flow.

Researchers and physicians investigating the condition of patients suffering from heart or circulatory impairment are usually interested in both the quantitative total net forward blood flow and in the blood flow waveform, plotted as a function of time. The total net forward flow is a measure of the blood perfusing the limb during one complete heart cycle. The blood flow waveform, on the other hand, is useful for analyzing various dynamic characteristics of the circulatory system. For greatest usefulness, it is important that the waveform provide quantitative information, including an accurate zero-flow level.

2. Description of the Prior Art

Non-invasive blood flowmeters of the type described in U.S. Pat. No. 3,659,591; No. 3,759,247; and No. 3,809,070 (assigned to the assignee of this invention) have many advantages stemming from the use of sensing electrodes placed on the skin instead of subcutaneously by surgical implantation. However, offset voltages are developed between the electrode surfaces and the skin. These offset voltages tend to drift with time and mask the signal contribution of steady flow components. Consequently, such instruments are not responsive to steady flow, only to variations in flow rate, which is the pulsatile part of the flow. In fact, the non-invasive, constant-magnetic-field type of blood flowmeter perceives the residual flow amplitude during the post-diastolic period as a "pulsatile zero" reference. The indicated total net flow per full cycle, therefore, may be less than the actual systolic forward portion of the pulsatile flow component. In other words, the previously mentioned drift problems prevent determination of the true zero flow level on the blood flow waveform produced by such a flowmeter.

SUMMARY OF THE INVENTION

It is the principal object of the present invention to provide a method and apparatus for modifying the blood flow in a limb of a living being such that a flowmeter, responsive only to modulated flow, will measure the total net blood flow in the limb, and in particular, will measure the total net forward arterial flow and will add to an arterial blood flow waveform the information for an accurate zero flow level.

A further object of the invention is to provide a method and apparatus for converting the non-modulated residual component of an arterial flow pattern into an equivalent volume of fully pulsatile flow which can be sensed by a non-invasive, constant-magnetic-field type of flowmeter.

Another object of the invention is to provide a method and apparatus for periodically occluding blood vessels in a limb to provide a true zero flow reference and to permit continuously varying blood flow through said vessels between successive occlusion periods.

These and other objects are achieved by a method for measuring blood flow through a limb of a living being which includes the steps of:

(a) periodically occluding blood vessels at a predetermined location along a limb of a living being to stop the flow of blood through said vessels for a predetermined period of time;

(b) permitting nonconstant blood flow through said vessels during each interval between successive occlusions;

(c) detecting the nonconstant flow through said blood vessels; and (d) processing said detected signal to obtain the total flow of blood through said blood vessels.

Preferably, the step of detecting the blood flow includes imposing a steady magnetic field, transversely to the limb, of an intensity strong enough to produce detectable electric signals on the skin of the limb in the vicinity of said periodically occluded blood vessel proportional to the blood flow, and placing a plurality of electrodes in circumferentially spaced relation on the skin of the limb adjacent to the periodically occluded location.

Preferably, the step of periodically occluding a blood vessel or vessels comprises applying pressure to the limb at said predetermined location, the pressure being sufficient to occlude the blood vessels for said predetermined period of time. The pressure desirably is applied uniformly around the circumference of the limb.

If the selected blood vessels are arteries, it has been found that the indicated net blood flow rate increases with increasing cuff pressure up to the local diastolic pressure. As cuff pressure exceeds the local diastolic pressure, the net forward flow per heart cycle decreases. Consequently, the pressure should equal or slightly exceed the diastolic pressure at the point of application. This will occlude the arterial vessels in the limb during the diastolic and post-diastolic portions of each heart cycle. Since the latter is the portion during which the residual forward flow occurs, such flow will be eliminated.

The pressure can be applied either steadily through the selected number of heart cycles or intermittently during only the diastolic and post-diastolic portions of each heart cycle and released during the systolic portion. In the former case, the applied pressure should no more than slightly exceed the diastolic pressure, thereby permitting fully pulsatized arterial inflow past the restricted location in response to the substantially greater blood pressure during the systolic portion of each heart cycle.

The processing steps typically include cumulatively storing the pulsatized signal output to provide a time-integrated signal, which is then divided by the measuring time to yield a signal proportional to the average arterial blood flow rate into the limb. Because the circulatory system adjusts to maintain almost the same total net blood flow rate to the distal part of the limb, the integrated and time-divided signal from the modified (fully pulsatized) blood flow pattern will be essentially equal to the actual total net forward flow rate under unmodified conditions.

Since the unmodified flow pattern includes both forward and retrograde flow, and since the non-invasive flowmeter of the type described above normally will not provide an accurate zero flow indication, the processed signal from the modified blood flow pattern has an amplitude greater than an equivalent signal from the unmodified flow pattern by an amount approximately equal to the average value of the residual flow rate during the same period.

Thus, a further aspect of the method of this invention comprises cumulatively storing (i.e., integrating) a series of unmodified blood flow signals (with no pressure on the limb), cumulatively storing a series of fully pulsatized blood flow signals (with pressure applied sufficient to occlude the arterial vessels during each diastolic and post-diastolic period), time-dividing each integrated series of signals, and subtracting the former result from the latter. The resulting value can then be applied to conventional blood flow waveform display apparatus to provide an accurate indication of the zero flow baseline.

Still another aspect of the method of this invention involves using the above-mentioned discovery (that maximum pulsatile blood flow occurs when the cuff is inflated to diastolic pressure) as a basic for determining local diastolic pressure in a limb. This pressure is often difficult or impossible to determine accurately by the conventional auditory method using a stethoscope, when the blood pressure is low. Hence, this aspect of the invention comprises incrementally increasing the cuff pressure, detecting the flow, and determining the pressure at the indicated maximum pulsatile flow.

The pressure invention also includes apparatus for performing the described method. The apparatus is a combination of a conventional blood flow measuring system and means adapted to apply uniform predetermined pressure around the circumference of a limb of a living being for at least a portion of each heart cycle. The pressure applying means may include a pressure cuff of the type used in a conventional sphygmomanometer, a source of air under pressure, and air supply and exhaust lines equipped with valves for selectively inflating and deflating the pressure cuff.

An embodiment of such apparatus, specifically adapted to automatically apply pressure around the limb during the diastolic and post-diastolic portion and release the pressure during the systolic portion of each heart cycle, includes a trigger circuit actuated by the R-wave of an electrocardiac signal sensed at a suitable location of the skin of the living being (the R-wave being the sharply peaked portion of an electrocardiogram). The trigger circuit actuates first and second delay generators which delay the trigger pulse until the onset of the next ensuing diastolic and systolic periods, respectively. The resulting first and second delayed trigger pulses then actuate first and second duration generators which create first and second timing pulses related in length to the diastolic and post-diastolic portion of each heart cycle, on the one hand, and the systolic portion of each heart cycle, on the other hand. Finally, the first and second timing pulses actuate valve driver circuits for opening the air supply valve during the diastolic and post-diastolic period and the exhaust valve during the systolic period, respectively.

The foregoing and other features of the present invention will be described in greater detail in connection with the preferred embodiments illustrated in the accompanying drawings.

DESCRIPTION OF THE PREFERRED EMBODIMENTS

Figure 1:
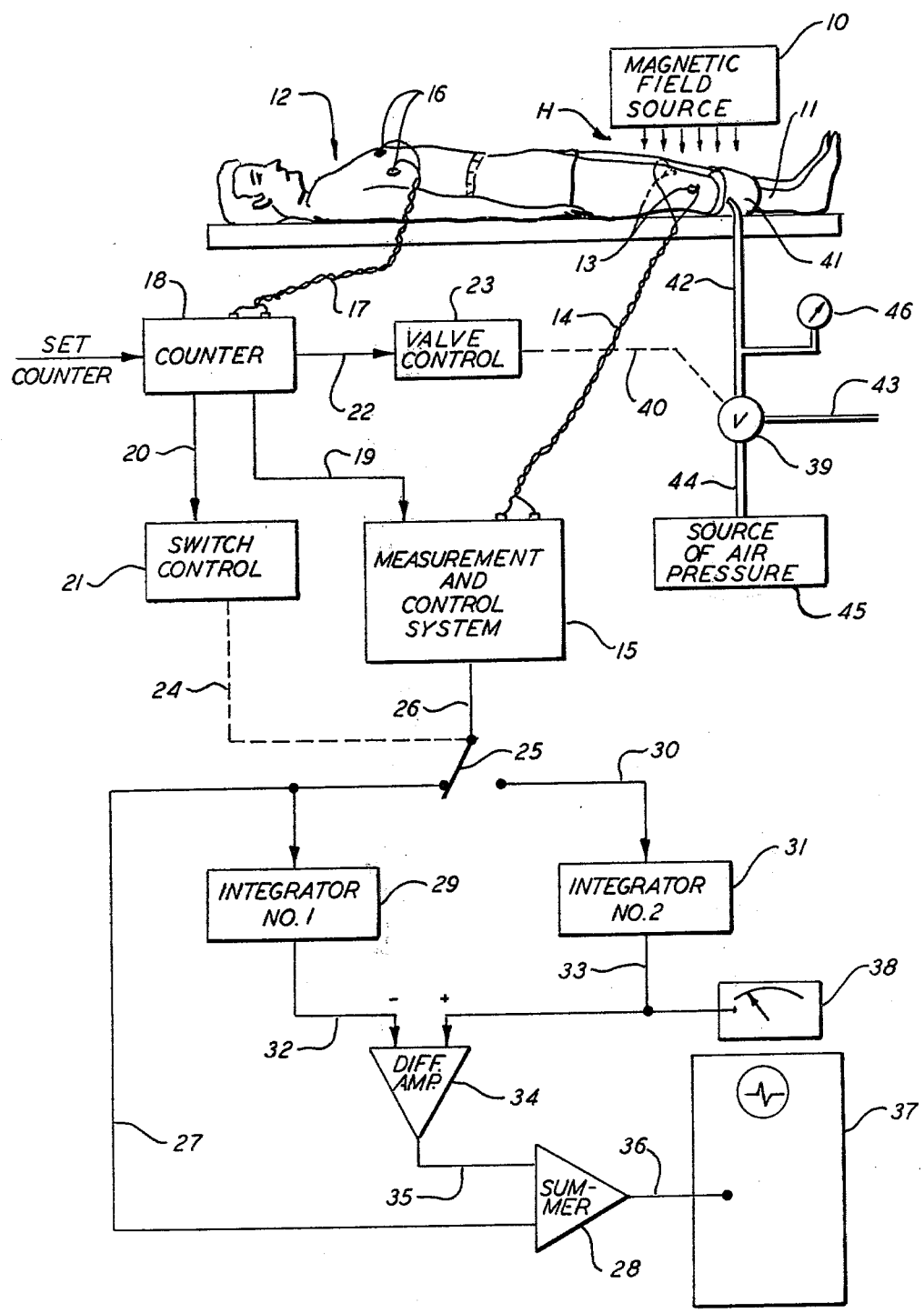
FIG. 1 illustrates in block diagram form a preferred embodiment of apparatus for measuring fully pulsatized blood flow in a limb of a living being.

Referring to FIG. 1, apparatus for performing the method of the invention includes a non-invasive blood flowmeter having a source 10 of a steady magnetic field having sufficient strength to produce detectable electric signals on the skin of a limb 11 of a living subject 12 in response to blood flow in the limb. The magnetic source may be a direct current electromagnet or a permanent magnet which can be positioned so that the magnetic field H is directed transversely to the limb.

At least two first sensing means, in the form of electrodes 13, are positioned in circumferentially spaced relation on the skin of the limb within the magnetic field for detecting the blood flow signals in selected blood vessels according to known techniques. The measuring electrodes are connected through twisted leads 14 to a conventional measurement and control system 15. System 15 may be of the type disclosed in the previously mentioned U.S. Pat. No. 3,659,591, No. 3,759,247, and No. 3,809,070. Such a system includes circuits for cumulatively storing successive blood flow waveforms over a number of heart cycles to provide an averaged blood flow signal having random and extraneous noise components reduced to insignificant levels.

In order to provide synchronizing and timing or clocking signals to the measurement and control system, a pair of second sensing means, in the form of auxiliary electrodes 16 are connected by a pair of twisted leads 17 to an adjustable counter 18. The auxiliary electrodes are placed on the skin of the subject at a location where a strong electrocardiac signal can be obtained. The counter produces a synchronizing signal once each heart cycle in response to the electrocardiac signal, the synchronizing signal being transmitted over connecting line 19 to the measurement and control system. In addition, the counter is set to deliver a timing or control pulse, after counting a selected number of heart cycles, over a connecting line 20 to a switch control 21 and over a connecting line 22 to a valve control 23.

Switch control 21 is physically connected, as shown by dashed line 24, to a switch 25 in the output line 26 from the measurement and control system for shifting the switch alternately between a first position and a second position in response to successive timing signals from the counter. In its first position, switch 25 directs the output of the measurement and control system over a connecting line 27 to one input of a summing circuit 28 and to a first integrating circuit 29. In its second position, switch 25 directs the output of the measurement and control system over a connecting line 39 to a second integrating circuit 31.

The outputs of the first and second integrating circuits are directed over respective connecting lines 32 and 33 to a differential amplifier 34, where the amplitude of the output of the first integrator is subtracted from the amplitude of the output of the second integrator. The resulting difference signal is delivered to another input of the summing circuit via connecting line 35. The output of summing circuit 28 is directed via connecting line 36 to a waveform display device 37. In addition, the output signal from the second integrator is fed via connecting line 33 to a signal amplitude display device 38.

Simultaneously with the switching of the measurement and control system output between the first and second integrators, valve control 23 actuates a valve 39, through a physical connection indicated by dashed line 40, to move between respective first and second positions. In its first position, valve 39 connects a pressure cuff 41, which surrounds limb 11 at or slightly distal from the location of measuring electrodes 13, through tubing 42 to an exhaust line 43, which may terminate either in the open atmosphere or in a vacuum reservoir (not shown). In its second position, valve 39 connects the pressure cuff 41 through tubing 44 to a source of air pressure 45. The pressure in the cuff is indicated in each case by a gauge 46.

The operation of the apparatus of FIG. 1 will be described in connection with the arterial blood flow waveforms shown in FIGS. 2 and 3. At the commencement of operation, the counter is set for the desired number of heart cycles to be accumulated and processed during each phase of the measurement process. An initiating signal from the counter actuates switch 25 to connect the output of measurement and control system 15 to first integrator 29 and also directly to summing circuit 28 and thence to waveform display device 37. A simultaneous initiating signal actuates valve 39 to connect pressure cuff 41 to exhaust line 43; so that no constricting pressure is exerted on the limb. Switch 25 and valve 39 remain in these respective positions until the selected number of blood flow waveform cycles have been entered into the measurement and control system from the first sensing means 13.

Figure 2:
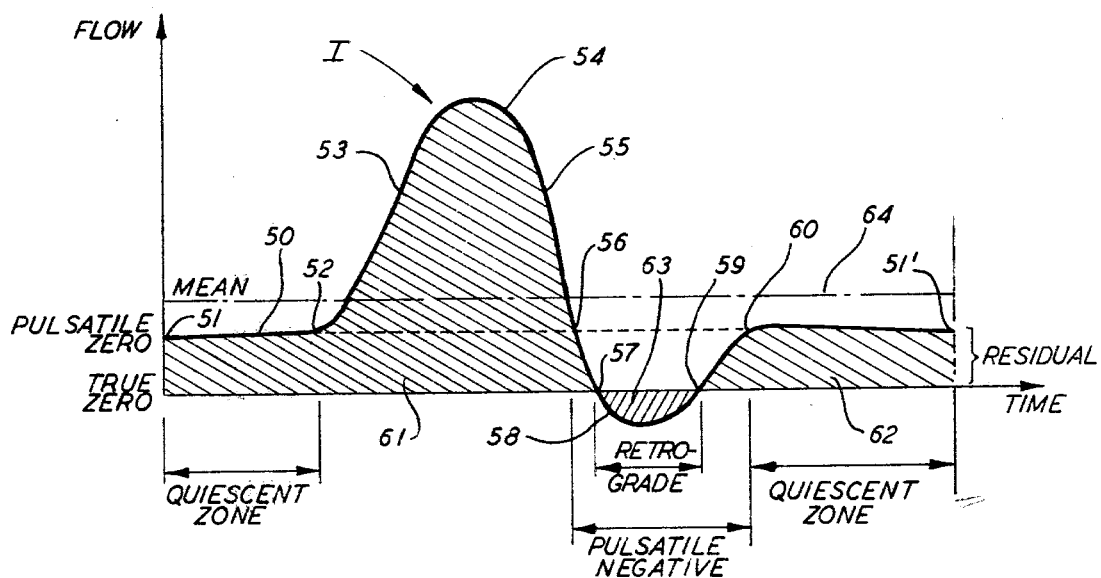
FIG. 2 represents a typical unmodified arterial blood flow pattern in a limb.

FIG. 2 depicts a normal unrestricted arterial blood flow waveform, with instantaneous flow rate plotted as a function of time, as it would appear on display device 37. It will be appreciated that, because of extraneous noise pickup, the actual waveform display will begin to approach the form of FIG. 2 only after a number of heart cycles have been averaged in the measurement and control system. The averaging period preferably extends for about one minute.

In the figure, forward flow (i.e., outward from the heart to the extremity of the limb) is plotted above the true zero flow baseline, and negative, or retrograde, flow is plotted below the true zero flow baseline. As explained earlier, however, the offset voltages developed between the skin and the measuring electrodes prevent determination of the true zero flow point on the ordinate of the flow waveform display 37. In all other respects, the waveform of FIG. 2 is representative of a typical waveform that would appear on the display 37.

In particular, starting at the ordinate, the waveform shows a period of relatively constant flow 50 from point 51 to point 52. This represents the residual flow during the postdiastolic period of a heart cycle. Since the start of the flow waveform display is synchronized by a pulse from counter 18 corresponding to the R-wave of the electrocardiac signal from the second sensing electrodes, the time between points 51 and 52 represents the delay for the pressure pulse from the heart to reach the location of the measuring electrodes on the limb.

The post-diastolic portion of the local flow waveform ends at 52 with the commencement of sharply rising portion 53 which reaches a peak at point 54 and then falls continuously through portion 55 past point 56 to the true zero flow baseline at point 57. Points 52 and 56 correspond to the initiation and termination, respectively, of the systolic period of each heart cycle.

Following the systolic period and during the ensuing diastolic period, there may be a short interval of retrograde flow 58, between points 57 and 59, before the flow again rises to the residual flow level at point 60, where it remains for the rest of the heart cycle (the post-diastolic period) until point 51', which corresponds to point 51 at the commencement of the waveform. The cycle then repeats itself.

The period of residual flow is also known as the quiescent zone, and the amplitude of the residual flow is termed the "pulsatile zero" level, since the positive and negative pulsatile portions of the waveform appear to rise and fall, respectively, from this level. Moreover, integration in the first integrator 29 of this waveform from the output of measurement and control system 15 for the unrestricted flow condition represented by FIG. 2 will yield a value based on the pulsatile zero flow level rather than on true zero flow. As a result, the mean forward flow indicated by the output of integrator 29 will be less than the true mean forward flow by an amount equal to the value of the residual flow.

In other words, the true total net forward flow per heart cycle is the algebraic sum of the positive areas 61 and 62 and the negative area 63 shown in FIG. 2. The valve of this algebraic sum divided by the time of one heart cycle is equal to the mean or average arterial flow in the limb, as indicated by horizontal line 64. That is to say, the algebraic sum of areas 61, 62, and 63 is equal to the area under mean line 64.

Because the flowmeter is unable to determine the true zero flow level, first integrator 29 will actually determine the algebraic sum of the positive area under the systolic flow curve from points 52 to 56 on the "pulsatile zero flow" level and the "negative" area above the curve from point 56 to point 60. This algebraic sum is obviously less than the true total net flow by an amount equal to the area under the mean flow line 64.

After the selected number of heart cycles have passed through counter 18, the counter transmits simultaneous trigger pulses to switch control 21 and valve control 23. Switch control 21 then actuates switch 25 to move to its second position where it connects the output of the measurement and control system to the input of second integrator 31, and valve control 23 at the same time moves valve 39 so that it connects pressure cuff 41 with pressurized air source 45 and closes the exhaust passageway.

The pressure of source 45 is adjusted rapidly to provide a pressure in the cuff equal to or slightly exceeding the diastolic pressure of the subject at the location of the cuff, as determined by conventional techniques. This pressure can be checked by means of gauge 46. Under the influence of the pressurized cuff, which exerts a constricting pressure uniformly around the circumference of the limb, the arterial vessel is occluded during the diastolic and post-diastolic portions of each heart cycle. Therefore, during the quiescent period of the arterial pressure cycle, no flow can pass through the artery. The condition is shown in FIG. 3, which is a blood flow waveform of the arterial flow after the cuff has been pressurized.

Because of this mechanical interruption of the arterial hydraulic system, there is a known and true "zero" value of the flow during at least some portion of the quiescent part of the flow cycle. Thereafter, the systolic pressure wave originating from the heart and the aorta is sufficient to overcome the counterpressure of the cuff and forces the opening of the arterial vessel for as long as the systolic pressure pulse lasts. The flow of blood resumes through the artery until the pressure in the artery on the heart side of the cuff falls back to its diastolic value, while venous return flow remains obstructed by the cuff pressure.

To better understand the hydraulic phenomenon, one can assume that the instantaneous pressure values in the artery on the proximal side (i.e., the heart side) of the cuff are essentially the same as the central pressure values. The arterial pressure on the distal side of the cuff at the time of the systolic peak is also the same as the central systolic pressure, minus a small pressure loss through the few inches of restriction of the arterial vessel due to the pressurized cuff.

After the passage of the blood pressure wave and return to the diastolic value, the artery is obstructed again by the equal or slightly greater pressure in the cuff. From the moment of occlusion the elasticity of the arterial network on the distal side of the cuff continues to produce a steady flow to the arterioles and thence to the veinules, thus increasing the pressure of the venous network on the distal side of the cuff. This happens until the end of the occlusive quiescent period. The venous counter-pressure on the distal side of the cuff is not significantly increased, however, because of the limited duration of cuff operation.

During the diastolic quiescent period the arterial system on the distal side of the cuff loses pressure, as it is not being resupplied from the central network. At the moment of reopening the restriction, this depleted distal arterial network must be refilled. This creates an additional demand on the pulsatile systolic flow. Consequently, this systolic flow has been found to become larger upon pressurization of the cuff than it was with the cuff unpressurized.

Figure 3:
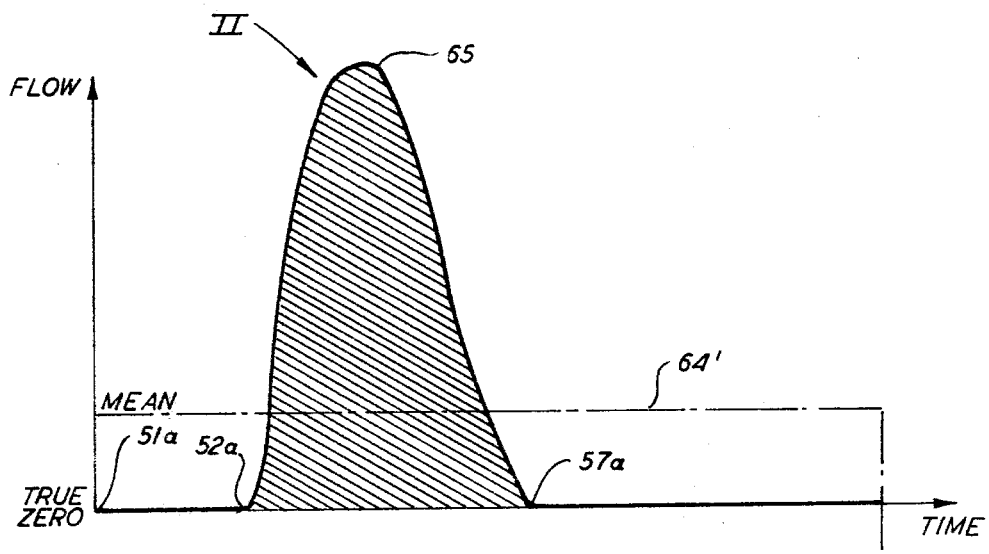
FIG. 3 represents a wholly pulsatized arterial blood flow pattern obtained by the method and apparatus of the invention.

This increase is illustrated by the substantially larger peak flow value 65 in FIG. 3, compared with the peak flow value 54 of the unrestricted blood flow waveform of FIG. 2. As a result of this increased systolic flow, the average net forward flow over one complete heart cycle, as indicated by mean flow line 65' is at a level comparable to the mean flow line 64 for the unrestricted flow waveform of FIG. 2.

Because all the arterial flow to the limb under the conditions of FIG. 3 is modulated (i.e., the flow is "totally pulsatized"), and a true "zero flow" reference line is known, a pulsatile flowmeter of the type in FIG. 1 will measure the totality of the flow. Consequently, the output of second integrator 31 is approximately equal in value to the true total net forward flow under unrestricted conditions, because the local regulation capabilities of the limb on the distal side of the restriction are such that the total perfusion of blood to the distal side of the limb is maintained nearly constant both before and during the period of cuff pressurization. This value is displayed on meter 38 and also is transmitted to the other input of differential amplifier 34. Within differential amplifier 34 the output 32 of first integrator 29 is subtracted from the output 33 of second integrator 31 to provide an output equal to the integrated value of the steady flow or residual flow component of the unrestricted blood waveform of FIG. 2.

Thus, the steady value generated by differential amplifier 34 and the fully pulsatized signal from line 27 are summed in circuit 28 and merged in display 37, which shows the true total flow waveform with a true zero flow baseline.

The relation between the steady flow and modulated flow components of the unrestricted flow waveform (waveform I) of FIG. 2 and the wholly pulsatized flow waveform (waveform II) of FIG. 3 can be expressed in mathematical symbols as follows:

$$\int_0^T (\text{steady flow I} + \text{modulated flow I}) \, dt = K \int_0^T (\text{modulated flow II}) \, dt,$$

where K is a factor ($\approx 1.1$) to account for reduced flow due to the cuff restriction, where the period of integration T is the same in both cases. The two integrators and the comparator solve this equation for the value of the residual flow component:

$$\int_0^T (\text{steady flow I}) \, dt = K \int_0^T (\text{modulated flow II}) \, dt - \int_0^T (\text{Modulated flow I}) \, dt$$

The integrated value on the left side of the equation is then applied to the display apparatus 23 where, by use of conventional circuits and techniques, an accurate zero flow baseline can be presented on the display of the unrestricted flow waveform provided by measurement and control system 15 over connecting line 27 when switch 25 is in its first position.

In the foregoing description, the signals dealt with are time-integrated signals. Thus, their amplitude is a function of the time of integration. So long as the time of integration is the same for the modified and unmodified blood flow signals, these can be subtracted according to the described procedure. Since the rate of blood flow is ultimately desired, however, the actual equipment includes integrating circuits having conventional time dividing networks; so that the output signal is proportional to the average rate of flow. In this way, it is not necessary that the processing times for the modified (pulsatized) blood flow signals be the same as the processing time for the unmodified blood flow signals.

As indicated previously, the venous counter-pressure on the distal side of the cuff is not significantly increased during the limited period of cuff pressurization. Since the average heart beats in the range of from 60 to 100 beats per minute, a cumulation of individual blood flow waveforms over a period of no more than one to three minutes will usually provide an averaged signal substantially free from extraneous noise. It is possible with an alternative embodiment of cuff pressurizing apparatus, however, to eliminate even the small venous pressure buildup that may occur during the time required to obtain a noise-free averaged waveform display.

Figure 4:
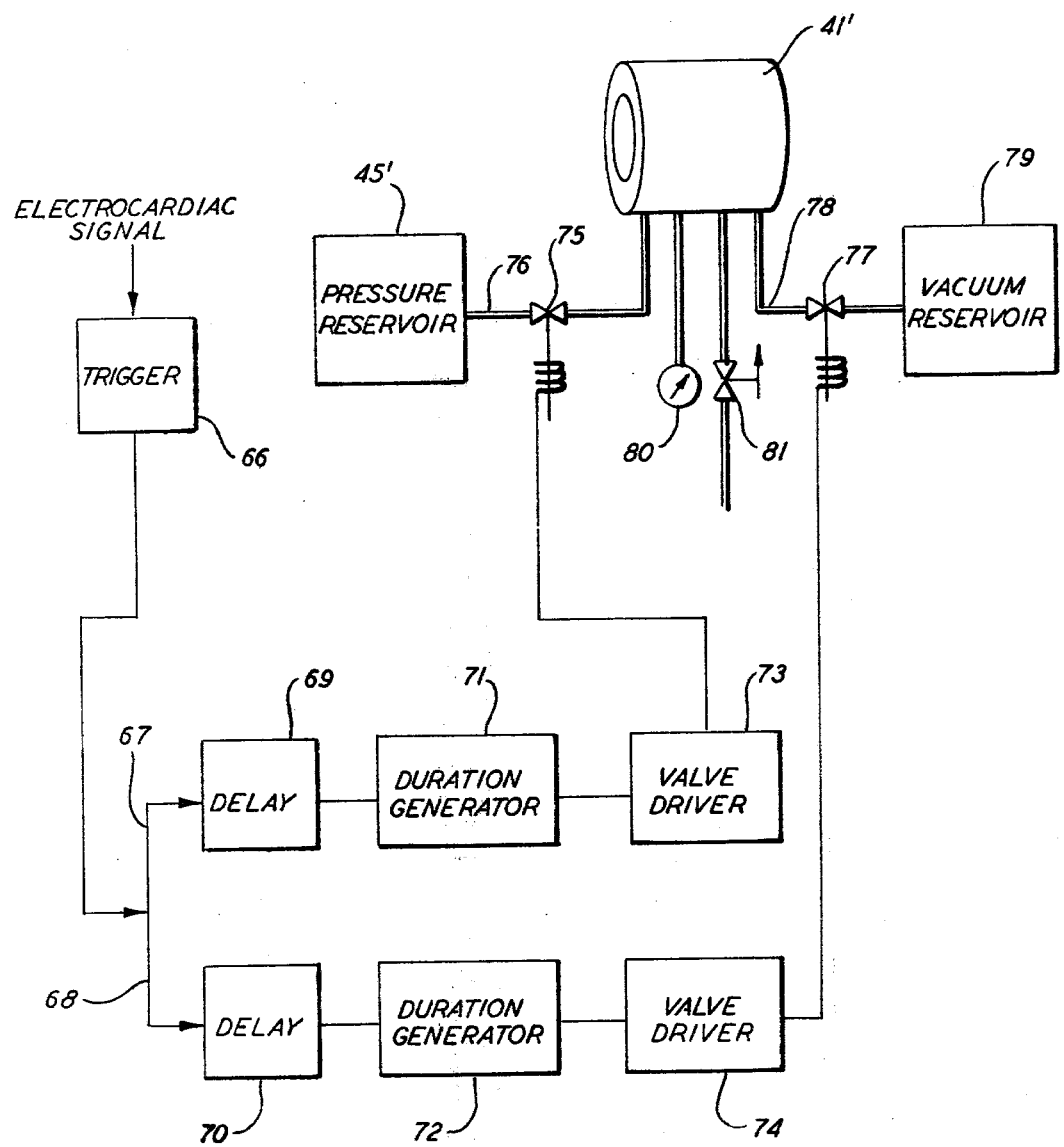
FIG. 4 illustrates in block diagram form an alternative automatic pressure applying apparatus according to the invention.

Referring to FIG. 4, one such apparatus includes a trigger circuit 66, such as a conventional Schmitt trigger, which is adapted to produce a sharp triggering pulse in response to the R-wave of each electrocardiac signal, as may be provided by the auxiliary electrodes 16 of FIG. 1. The triggering pulse from circuit 66 is fed over connecting lines 67 and 68 to first and second valve actuating circuits comprising pulse delay circuits 69 and 70, timing pulse duration generators 71 and 72, and valve drivers 73 and 74, respectively.

The output of valve driver 73 actuates a valve, such as solenoid valve 75, located in supply pipe 76 leading from a pressure reservoir 45' to a pressure cuff 41', the pressure reservoir and cuff being similar to reservoir 45 and cuff 41 of FIG. 1. The output of valve driver 74 actuates a similar valve 77 installed in an exhaust pipe 78 leading from cuff 41' to a vacuum reservoir 79. Alternatively, the exhaust line may lead directly to the open atmosphere, as in the embodiment of FIG. 1, and vice-versa. The advantage of exhausting to a vacuum reservoir is that more rapid and positive cuff pressure release is obtained than when exhausting to the atmosphere.

Pressure cuff 41' may also be provided with a pressure gauge 80 and an adjustable relief valve 81, which preferably is set to open at a pressure slightly above the measured diastolic pressure of the subject.

In operation, the pressure cuff apparatus of FIG. 3 is applied to a living being in the same manner as the pressure cuff apparatus illustrated in FIG. 1, with all other necessary components of the FIG. 1 system being included. Trigger circuit 66, for example, should be coupled to auxiliary electrodes 16 to obtain an electrocardiac signal for synchronizing and clock purposes. Pressure cuff 41' is wrapped around the limb to be measured at, or on the distal side of, the location of measuring electrodes 13.

Trigger circuit 66 produces a pulse in synchronism with the R-wave of each heart cycle. In delay circuit 69 this pulse is delayed for a chosen period which may be equal, for example, to the time from the R-wave to the completion of the corresponding systolic flow waveform at the measurement location. This is equivalent to the time from point 51a to point 57a on the waveform of FIG. 3. The delayed pulse from circuit 69 then actuates timing pulse duration generator 71, which may be a conventional monostable multivibrator. Generator 71 produces a timing pulse for actuating valve driver 73, the duration of the pulse being equal to the duration of the diastolic and post-diastolic period of each heart cycle. Delay circuit 69 is optional, however, and the signal from trigger 66 may be coupled directly to duration generator 71, if desired.

Valve 75 is normally shut, and the timing pulse from generator 71 causes it to open, thereby pressurizing the cuff for the length of each successive diastolic and post-diastolic period. At (or before) the end of each such period, the first timing pulse ceases, and valve 75 shuts. If there are no leaks in the cuff pressurizing system, the first timing pulse need only be long enough to charge the cuff to the desired pressure, after which valve 75 can be allowed to shut.

The second valve actuating circuit operates in a similar manner except that delay circuit 70 provides a delay from the R-wave to the commencement of the next ensuing systolic flow waveform. This is equivalent to the time from point 51a to point 52a on the waveform of FIG. 3. Duration generator 72 then provides a timing pulse having a duration equal to or less than the systolic period of each heart cycle (equivalent to the time between point 52a and point 57a in FIG. 3). The minimum length of the timing pulse from duration generator 72 must be at least long enough to exhaust the pressurizing air in the cuff.

The timing pulse from generator 74 thereby actuates valve 77 (also a normally shut valve) to open during the systolic portion of each blood flow waveform. Thus, the apparatus of FIG. 3 operates to automatically and alternately open pressure supply valve 75 during the diastolic and post-diastolic flow period of each heart cycle and exhaust valve 77 during the systolic period of each cycle. Because all cuff pressure is released during the systolic period of each flow cycle, any venous counter-pressure that was developed during the preceding period of cuff pressurization will be dissipated.

The apparatus of FIG. 1 may be used to practice the method, referred to in the Summary, of determining the local diastolic pressure by measuring the blood flow. In particular, this aspect of the method comprises adjusting the cuff pressure, by means of relief valve 81, by incremental steps from below minimum normal diastolic pressure to above maximum diastolic pressure. For each incremental pressure, the total net arterial blood flow is measured, according to the procedure described above. The pressure at which the flow reading is a maximum is then equal to the actual local diastolic pressure.

It will be appreciated that other equivalent apparatus can be used to perform the method disclosed in this application without departing from the scope of the present invention. In particular, it will be appreciated that the method of creating fully pulsatized blood flow can be used with other types of blood flow measuring apparatus, such as Doppler flow meters, for example.

What is claimed is:

1. A method for measuring blood flow in a limb of a living being comprising:
    (a) periodically occluding the arterial blood vessels at a predetermined location along a limb of a living being to stop the flow of blood through said vessels, the duration of each occlusion being approximately coincident with the diastolic and post-diastolic period of a corresponding heart cycle of the living being;
    (b) permitting a nonconstant unidirectional blood flow pulse through said arterial vessels during each interval between successive occlusions, each interval being approximately coincident with the systolic period of a heart cycle of the living being;
    (c) detecting signals proportional to the nonconstant pulsatile flow through said arterial blood vessels during a predetermined plurality of said intervals; and (d) processing said detected signals to obtain the time-integrated total flow of blood through said arterial blood vessels for the detecting period.

2. A method for measuring blood flow in a limb of a living being comprising:
(a) applying presssure at a predetermined location along a limb of a living being for a predetermined period of time, said pressure being at least equal to and no more than slightly exceeding the diastolic pressure at said location, to stop the flow of blood through arterial vessels in the limb by occluding said arterial vessels when their internal pressure is less than said applied pressure;
(b) permitting nonconstant blood flow through said arterial vessels during each interval between successive occlusions;
(c) detecting the amplitude of signals proportional to the nonconstant flow rate through said arterial blood vessels during each interval between a plurality of successive occlusions; and
(d) processing said detected signals to obtain the total flow of blood through said arterial blood vessels during the time spanned by said successive occlusions.

3. A method for measuring blood flow in a limb of a living being comprising:
(a) periodically applying uniform pressure around the circumference of a limb of a living being at a predetermined location along said limb, said pressure being at least equal to the diastolic pressure at said location and being applied only during the diastolic and post-diastolic portion of each of a plurality of successive heart cycles of the living being, to stop the flow of blood through arterial vessels in the limb during said diastolic and post-diastolic portion of each heart cycle;
(b) releasing the pressure during the systolic portion of each heart cycle to permit a nonconstant unidirectional blood flow pulse through said arterial vessels during said systolic portion of each heart cycle;
(c) detecting signals proportional to the nonconstant flow pulses through said arterial blood vessels; and
(d) processing said detected signals to obtain a time-averaged flow rate of blood through said blood vessels over said plurality of successive heart cycles.

4. A method for measuring blood flow in a limb of a living being comprising:
(a) periodically applying uniform pressure around the circumference of a limb of a living being at a predetermined location along said limb, said pressure being at least equal to the diastolic pressure at said location and being applied only during the diastolic and post-diastolic portion of each of a plurality of successive heart cycles of the living being; to stop the flow of blood through arterial vessels in the limb during said diastolic and post-diastolic portion of each heart cycle;
(b) releasing the pressure during the systolic portion of each heart cycle to permit a nonconstant unidirectional blood flow pulse through said arterial vessels during said systolic portion of each heart cycle;
(c) detecting signals proportional to the nonconstant flow pulses through said arterial blood vessels; and
(d) cumulatively storing said detected signals for a predetermined period of time corresponding to said plurality of successive heart cycles to obtain a time-integrated signal proportional to the total flow of arterial blood at said location during the predetermined time.

5. A method for measuring blood flow in a limb of a living being comprising:
(a) applying uniform pressure around the circumference of a limb of a living being at a predetermined location along said limb, said pressure being at least equal to the diastolic pressure and substantially less than the systolic pressure at said location and being applied continuously for a predetermined period of time equal to at least a plurality of heart cycles of the living being, thereby occluding the arterial blood vessels in the limb during the diastolic and post-diastolic portion of each heart cycle during said predetermined period of time while permitting nonconstant blood flow through said arterial vessels during each interval between successive occlusions;
(b) sensing the amplitude of signals proportional to the nonconstant flow through said arterial blood vessels; and
(c) processing said sensed signals to obtain the average flow rate of blood through said arterial blood vessels during said predetermined period of time.

6. A method for measuring blood flow in a limb of a living being comprising:
(a) applying uniform pressure around the circumference of a limb of a living being at a predetermined location along said limb, said pressure being at least equal to the diastolic pressure and substantially less than the systolic pressure at said location and being applied continuously for a predetermined period of time equal to at least a plurality of heart cycles of the living being, thereby occluding the arterial blood vessels in the limb during the diastolic and post-diastolic portion of each heart cycle during said predetermined period of time while permitting nonconstant blood flow through said arterial vessels during each interval between successive occlusions;
(b) sensing the amplitude of signals proportional to the nonconstant flow through said arterial blood vessels; and
(c) cumulatively storing the sensed signals over said predetermined period of time to provide a time-integrated signal proportional to the average arterial blood flow at said location for said predetermined period of time.

7. A method for measuring blood flow in a limb of a living being comprising:
(a) detecting signals proportional to the blood flow through arterial blood vessels at a predetermined location on a limb of a living being;
(b) cumulatively storing the signals detected in step (a) for a selected number of heart cycles to provide a first timeintegrated signal proportional to the average net unrestricted arterial blood flow into the limb at said location;
(c) occluding the arterial blood vessels at said location during only the diastolic and post-diastolic portions of an additional number of heart cycles;
(d) cumulatively storing the signals detected during step (c) for said additional number of heart cycles to provide a second time-integrated signal proportional to the average arterial blood flow at said location; and (e) subtracting the second signal obtained in step (d) from the first signal obtained in step (b) to provide a third signal proportional to the average non-pulsatile residual arterial blood flow at said location.

8. A method for measuring blood flow in a limb of a living being comprising:
(a) detecting signals proportional to the blood flow through arterial blood vessels at a predetermined location on a limb of a living being;
(b) cumulatively storing the signals detected in step (a) for a selected number of heart cycles to provide a first timeintegrated signal proportional to the average net unrestricted arterial blood flow into the limb at said location;
(c) applying uniform pressure around the circumference of the limb at said location during at least the diastolic and post-diastolic portion of each heart cycle during an additional number of heart cycles, said pressure being equal to at least the diastolic pressure at said location so as to occlude the arterial blood vessels in the limb at said location during only the diastolic and post-diastolic portion of each heart cycle;
(d) detecting signals proportional to the blood flow through the arterial blood vessels during said additional number of heart cycles;
(e) cumulatively storing the signals detected during step (d) for said additional number of heart cycles to provide a second time-integrated signal proportional to the average arterial blood flow at said location; and
(f) subtracting the second signal obtained in step (e) from the first signal obtained in step (b) to provide a third signal proportional to the average non-pulsatile residual arterial blood flow at said location.

9. A method for measuring blood flow in a limb of a living being comprising:
(a) detecting signals proportional to the blood flow through arterial blood vessels at a predetermined location on a limb of a living being;
(b) cumulatively storing the signals detected in step (a) for a predetermined period of time to provide a first timeintegrated signal proportional to the average net unrestricted arterial blood flow into the limb at said location;
(c) applying uniform pressure around the circumference of the limb at said location during only the diastolic and postdiastolic portion of each heart cycle of the living being, said pressure being equal to at least the diastolic pressure at said location so as to occlude the arterial blood vessels in the limb at said location during the diastolic and post-diastolic portion of each heart cycle during an additional period of time;
(d) releasing the pressure around said limb during the systolic portion of each heart cycle during said additional period of time;
(e) detecting signals proportional to the blood flow through the arterial blood vessels in the limb during step (d);
(f) cumulatively storing the signals detected during step (e) for said additional period of time to provide a second time-integrated signal proportional to the average arterial blood flow at said location; and
(g) subtracting the second signal obtained in step (f) from the first signal obtained in step (b) to provide a third signal proportional to the average non-pulsatile residual arterial blood flow at said location.

10. A method for measuring blood flow in a limb of a living being comprising:
(a) detecting signals proportional to the blood flow through arterial blood vessels at a predetermined location on a limb of a living being;
(b) cumulatively storing the signals detected in step (a) for a selected number of heart cycles to provide a first timeintegrated signal proportional to the average net unrestricted arterial blood flow into the limb at said location;
(c) applying uniform pressure around the circumference of the limb at said location steadily during an additional number of heart cycles, said pressure being at least equal to and no more than slightly greater than the diastolic pressure at said location so as to occlude the arterial blood vessels during the diastolic and post-diastolic portion and to permit pulsatile arterial blood flow during the systolic portion of each of the additional number of heart cycles;
(d) detecting signals proportional to the blood flow through the arterial blood vessels during said additional number of heart cycles;
(e) cumulatively storing the signals detected during step (d) for said additional number of heart cycles to provide a second time-integrated signal proportional to the average arterial blood flow at said location; and
(f) subtracting the second signal obtained in step (d) from the first signal obtained in step (b) to provide a third signal proportional to the average non-pulsatile residual arterial blood flow at said location.

11. Apparatus for pulsatizing blood flow in a limb of a living being, the apparatus comprising:
a pressure cuff adapted to be wrapped around a limb of a living being at a predetermined location along the limb;
a source of air at a predetermined pressure connected to the cuff;
a first valve between the source of air pressure and the cuff for selectively inflating the cuff;
an exhaust line connected to the cuff;
a second valve in the exhaust line for selectively releasing air pressure from the cuff;
sensing means adapted to be placed on the skin of the living being at a location where a strong electrocardiac signal can be obtained for use as a synchronizing and timing signal;
a trigger circuit connected to the sensing means for providing a trigger pulse in synchronism with the R-wave of each heart cycle detected by the sensing means;
a first duration generator coupled to the output of the trigger circuit for producing a first timing pulse for opening the first valve long enough to attain said predetermined pressure in the cuff in response to the first trigger pulse;
a first valve driver connected between the output of the first duration generator and the first valve for opening the first valve for the duration of the first timing pulse;
a delay generator connected to the output of the trigger circuit for delaying each trigger pulse for a predetermined time until the onset of the next ensuing systolic period;
a second duration generator connected to the output of the delay generator for producing a second timing pulse for opening the second valve long enough to completely exhaust the pressure in the cuff in response to the delayed trigger pulse; and a second valve driver connected between the output of the second duration generator and the second valve for opening the second valve for the duration of the second timing pulse.

12. Apparatus for pulsatizing blood flow in a limb of a living being, the apparatus comprising:

a pressure cuff adapted to be wrapped around a limb of a living being at a predetermined location along the limb;

a source of air at a predetermined pressure connected to the cuff;

a first valve between the source of air pressure and the cuff for selectively inflating the cuff;

an exhaust line connected to the cuff;

a second valve in the exhaust line for selectively releasing air pressure from the cuff;

sensing means adapted to be placed on the skin of the living being at a location where a strong electrocardiac signal can be obtained for use as a synchronizing and timing signal;

a trigger circuit connected to the sensing means for providing a trigger pulse in synchronism with the R-wave of each heart cycle detected by the second sensing means;

a first delay generator connected to the output of the trigger circuit for delaying each trigger pulse for a predetermined time until the onset of the next ensuing diastolic period;

a first duration generator connected to the output of the first delay generator for producing a first timing pulse for opening the first valve long enough to attain said predetermined pressure in the cuff in response to the first delayed trigger pulse;

a first valve driver connected between the output of the first duration generator and the first valve for opening the first valve for the duration of the first timing pulse;

a second delay generator connected to the output of the trigger circuit for delaying each trigger pulse for a predetermined time until the onset of the next ensuing systolic period;

a second duration generator connected to the output of the second delay generator for producing a second timing pulse for opening the second valve long enough to completely exhaust the pressure in the cuff in response to the second delayed trigger pulse; and a second valve driver connected between the output of the second duration generator and the second valve for opening the second valve for the duration of the second timing pulse.

13. Apparatus for measuring blood flow in a limb of a living being, the apparatus comprising:

a pressure cuff adapted to be wrapped around a limb of a living being at a predetermined location along the limb;

a source of air at a predetermined pressure connected to the cuff, the pressure being sufficient to stop the flow of blood through blood vessels in the limb for a portion of a heart cycle of the living being;

a first valve between the source of air pressure and the cuff for selectively inflating the cuff;

an exhaust line connected to the cuff;

a second valve in the exhaust line for selectively releasing air pressure from the cuff;

first sensing means adapted to be placed adjacent to said means for applying pressure at a location suitable for detecting signals in response to blood flow in said blood vessels;

second sensing means adapted to be placed on the skin of the living being at a location where a strong electrocardiac signal can be obtained for use as a synchronizing and timing signal;

a trigger circuit connected to the second sensing means for providing a trigger pulse in synchronism with the R-wave of each heart cycle detected by the second sensing means;

a first delay generator connected to the output of the trigger circuit for delaying each trigger pulse for a predetermined time until the onset of the next ensuing diastolic period;

a first duration generator connected to the output of the first delay generator for producing a first timing pulse for opening the first valve long enough to attain said predetermined pressure in the cuff in response to the first delayed trigger pulse;

a first valve driver connected between the output of the first duration generator and the first valve for opening the first valve for the duration of the first timing pulse;

a second delay generator connected to the output of the trigger circuit for delaying each trigger pulse for a predetermined time until the onset of the next ensuing systolic period;

a second duration generator connected to the output of the second delay generator for producing a second timing pulse for opening the second valve long enough to completely exhaust the pressure in the cuff in response to the second delayed trigger pulse;

a second valve driver connected between the output of the second duration generator and the second valve for opening the second valve for the duration of the second timing pulse; and means connected to the first and second sensing means for processing the signals detected by the first sensing means for a predetermined number of heart cycles as detected by the second sensing means to produce a time-averaged blood flow signal.

14. Apparatus for measuring blood flow in a limb of a living being, the apparatus comprising:

a pressure cuff adapted to be wrapped around a limb of a living being at a predetermined location along the limb;

a source of air at a predetermined pressure connected to the cuff, the pressure being sufficient to stop the flow of blood through blood vessels in the limb for a portion of a heart cycle of the living being;

a first valve between the source of air pressure and the cuff for selectively inflating the cuff;

an exhaust line connected to the cuff;

a second valve in the exhaust line for selectively releasing air pressure from the cuff;

first sensing means adapted to detect blood flow in said vessels at said location;

second sensing means adapted to detect an electrocardiac signal of said living being for use as a synchronizing and timing signal;

a trigger circuit connected to the second sensing means for providing a trigger pulse in synchronism with the R-wave of each heart cycle detected by the second sensing means;

a first duration generator coupled to the output of the trigger circuit for producing a first timing pulse for opening the first valve long enough to attain said predetermined pressure in the cuff in response to the trigger pulse;

a first valve driver connected between the output of the first duration generator and the first valve for opening the first valve for the duration of the first timing pulse;

a delay generator connected to the output of the trigger circuit for delaying each trigger pulse for a predetermined time until the onset of the next ensuing systolic period;

a second duration generator connected to the output of the delay generator for producing a second timing pulse for opening the second valve long enough to completely exhaust the pressure in the cuff in response to the delayed trigger pulse;

a second valve driver connected between the output of the second duration generator and the second valve for opening the second valve for the duration of the second timing pulse; and means connected to the first and second sensing means for processing the signals detected by the first sensing means for a predetermined number of heart cycles as detected by the second sensing means to produce a time-averaged blood flow signal.

* * * * *